United States Patent [19]  [11] 4,013,712
Ragoonanan et al.  [45] Mar. 22, 1977

[54] PROCESS FOR MAKING ALKANE-1,2-DIOL DIESTERS

[75] Inventors: Dulcie Ragoonanan; Brian W. Harris, both of Trinidad, Trinidad And Tobago

[73] Assignee: Texaco Trinidad, Inc., Trinidad, Trinidad And Tobago

[22] Filed: Mar. 6, 1975

[21] Appl. No.: 555,917

[52] U.S. Cl. .......................................... 260/497 R
[51] Int. Cl.² .......................................... C07C 67/04
[58] Field of Search ...................... 260/497 R, 496

[56] References Cited

UNITED STATES PATENTS 3,403,175  9/1968  Wolgemuth ................... 260/497 R Primary Examiner—Anton H. Sutto
Assistant Examiner—Michael Shippen
Attorney, Agent, or Firm—T. H. Whaley; C. G. Ries; Henry W. Archer

[57] ABSTRACT

Disclosed is a controlled two stage process for converting 1-olefins to 1,2-diacetoxyalkanes. In the first stage, the olefins are oxidized to peroxides by preaerating the olefin with oxygen until the measured peroxide value has reached its maximum, then decreasing this value by 20 to 40%. In the second stage, the peroxides are decomposed by adding acetic acid and heating to a temperature of 120° C. in the absence of catalyst.

6 Claims, No Drawings

PROCESS FOR MAKING ALKANE-1,2-DIOL DIESTERS

BACKGROUND OF THE INVENTION

1. Field of the Invention

This invention relates to the preparation of 1,2-diacetoxyalkanes by the oxidation of aliphatic 1-olefins to peroxides with oxygen followed by decomposition of the peroxides in acetic acid solution in the absence of catalyst.

The product of the process of the invention find utility, inter alia, as oil additives, plasticizers, solvents and as intermediates in glycol manufacture.

2. DESCRIPTION OF THE PRIOR ART

The art to which the present process is aware of U.S. Pat. No. 3,542,857. In the process of that patent, olefins are oxidized with molecular oxygen in the presence of acetic acid and of cerium salts to form a mixture of vic-glycol monoesters and diesters. The use of cerium salts increases the cost of such a process as does the need to separate the products by fractional distillation, chromatography and the like.

The best results mentioned in this patent using a 1-octane feed is a 63.5% at 20.8% octene-1 conversion. With the present process, similar selectivity is achieved without any catalyst starting with decene-1 at 78.5% conversion.

British Pat. No. 904,304 and U.S. Pat. No. 3,271,447 also disclose one stage processes for the oxidation of olefinic compounds using various metal catalysts with or without hydrobromic acid.

SUMMARY OF THE INVENTION

The process of the invention comprises oxidizing with oxygen or an oxygen-containing gas a hydrocarbon monoolefin of the formula RCH = CH wherein R has from 5 to 20 carbon atoms. The maximum peroxide number of the olefin is determined in known manner by taking samples at intervals and reacting the potassium iodide in acetic acid and the liberated iodine is titrated with aqueous sodium thiosulfate solution. The oxidation is stopped when this value decreases by 20 to 40% from its maximum. At this point, acetic acid or another monocarboxylic alkanoic acid is mixed with the olefin and the reaction is continued at a temperature of 100°–120° C. until the PN (peroxide number) falls to a low level. At the end of the reaction any unreacted olefins and acid are distilled off.

In the practice of the invention, oxygen gas is introduced into the olefin and maybe diluted with an inert gas or can be used in the form of air. The oxygen rate may be in the range of about 0.5 to 100 liter/liter/hour, preferably in the range of about 20–40 liters/liter/hour. The process of the invention is conducted in the liquid phase and preferably an organic anhydride resistant to oxidation conditions is provided in the reaction medium. The preferred anhydride is acetic anhydride but other alkanoic acid anhydrides such as propionic anhydride are also suitable when used in the amount of 0–40% w/w.

The reaction temperature can vary from about 80° to 150° C. The reaction pressure preferably is atmospheric and the reaction temperature preferably ranges from about 100° to 120° C.

The invention is illustrated in a non-limiting fashion by the following examples.

EXAMPLES

In each run 1-decene was converted to 1,2-diacetoxy decane. In each case, oxygen was passed through a sintered disc at 0.5 liters/hour into the decene which has been heated to 140° C in a reactor. Samples were taken at intervals and the peroxide content determined. The plots of peroxide content with time showed a steady increase to a maximum after which the peroxide value decreased. When this value had decreased by 20 to 40%, the aeration was stopped, acetic acid was added and the reaction continued at 100°–120° C for the required time.

Further details are tabulated in the Table below.

DECOMPOSITION OF PRE-AERATED DECENE-1 IN ACETIC ACID WITH AND WITHOUT ACETIC ANHYDRIDE AND OXYGEN

| Run No. | Acetic Acid (g.) | Decene-1 (g.) | Decene-1 MPN | Acetic Anhydride (g.) | Oxygen l./hr. | Temp. °C. | Reaction Time (hrs.) | Decene-1 Conversion (%) | 1,2-Diacetoxy*decane (mole %) |
|---|---|---|---|---|---|---|---|---|---|
| A 40 | 262.5 | 20, | 405→260 | — | — | Reflux | 24 | 29 | 54.5 |
| 45 | 262.5 | 20, | 404→232 | — | — | Reflux | 24 | 30 | 54.0 |
| B 46 | 262.5 | 20, | 405→260 | — | 8 | 120 | 24 | 78.5 | 63.5 |
| 43 | 262.5 | 20, | 405→260 | 15 | 5 | 120 | 24 | 84 | 53.0 |
| 47 | 180 | 20, | 404→232 | 51 | 8 | 120 | 24 | 84.6 | 54.5 |
| 37 | 300 | 20, | 336→270 | 25.5 | 5 | 120 | 24 | 94 | 51 |

$$* - \text{Mole } \% = \frac{\text{Product}}{\text{MW of Product}} \times \frac{\text{MW of Decene}}{\text{Decene Converted}} \times 100$$

MPN = Maximum Peroxide Number (m.eq/1000g. sample)

It will be noted that the introduction of oxygen during the peroxide decomposition stage is beneficial. Thus in run 46 the decene reacted more completely than in runs 40 and 45 and the selectivity to the dioldiacetate was also higher. The addition of acetic anhydride to the reaction mixture (runs 43, 47 and 37) further increased the decene conversion but the reaction was slightly less selective.

Runs 40 and 45 show the effect of decomposing the peroxides in acetic acid without acetic anhydride under oxygen free conditions (no oxygen feed). The product was formed slowly — 30% conversion in 24 hours. The effect of adding acetic anhydride (runs 43, 47 & 37)

was to further increase the decene-1 conversion to 84–94% in 24 hours but at slightly reduced selectivity.

What is claimed is:

1. A liquid phase process for producing alkane-1,2-diol diesters in the absence of metal catalyst from an alkene of the formula:

$$RCH = CH_2$$

wherein R is an alkyl group having from 5 to 20 carbon atoms, comprising pre-aerating said alkene with an oxygen containing gas to form the corresponding peroxide; determining the maximum peroxide content of said alkene during aeration; terminating said aeration when said content has decreased from 20 to 40 percent from its maximum, decomposing said peroxide with a mono-carboxylic acid having from 1 to 6 carbon atoms; heating the resulting decomposition mixture to between 80° and 150° C. and recovering the diester product by distilling said acid and any unreacted olefin.

2. The process of claim 1 wherein said gas is passed through said alkene at a rate of 0.5 to 100 liters per liter of solution per hour.

3. The process of claim 1 wherein an alkanoic acid anhydride resistant to oxidation conditions is added to said decomposition mixture in an amount of up to 40 percent by weight thereof.

4. The process of claim 3 wherein said anhydride is acetic anhydride.

5. The process of claim 1, wherein said mixture is heated to between 100° and 120° C.

6. The process of claim 1 wherein said gas is passed through said alkene at a rate of about 20 to 40 liters per liter per hour.

* * * * *